US010206590B2

(12) United States Patent
Meriheinä

(10) Patent No.: US 10,206,590 B2
(45) Date of Patent: Feb. 19, 2019

(54) METHOD AND SYSTEM FOR MONITORING STRESS

(71) Applicant: MURATA MANUFACTURING CO., LTD., Nagaokakyo-shi, Kyoto (JP)

(72) Inventor: Ulf Meriheinä, Söderkulla (FI)

(73) Assignee: MURATA MANUFACTURING CO., LTD., Nagaokakyo-Shi, Kyoto (JP)

(*) Notice: Subject to any disclaimer, the term of this patent is extended or adjusted under 35 U.S.C. 154(b) by 600 days.

(21) Appl. No.: 14/807,067

(22) Filed: Jul. 23, 2015

(65) Prior Publication Data

US 2016/0022152 A1 Jan. 28, 2016

(30) Foreign Application Priority Data

Jul. 28, 2014 (FI) .................................... 20145694

(51) Int. Cl.
| | | |
|---|---|---|
| *A61B 5/0205* | (2006.01) | |
| *A61B 5/024* | (2006.01) | |
| *A61B 5/029* | (2006.01) | |
| *A61B 5/11* | (2006.01) | |
| *A61B 5/00* | (2006.01) | |
| *A61B 5/16* | (2006.01) | |
| *A61B 5/021* | (2006.01) | |

(52) U.S. Cl.
CPC ............ *A61B 5/0205* (2013.01); *A61B 5/029* (2013.01); *A61B 5/02405* (2013.01); *A61B 5/02416* (2013.01); *A61B 5/1102* (2013.01); *A61B 5/165* (2013.01); *A61B 5/4812* (2013.01); *A61B 5/02108* (2013.01); *A61B 5/1116* (2013.01)

(58) Field of Classification Search
CPC ... A61B 5/0205; A61B 5/165; A61B 5/02405; A61B 5/029; A61B 5/4812; A61B 5/1102; A61B 5/02416; A61B 5/1116; A61B 5/02108
See application file for complete search history.

(56) References Cited

U.S. PATENT DOCUMENTS

| 6,126,595 A | 10/2000 | Amano et al. |
| 9,044,147 B2 * | 6/2015 | Quinn ................ A61B 5/02225 |
| | | (Continued) |

FOREIGN PATENT DOCUMENTS

| JP | 2004223258 A | 8/2004 |
| JP | 2006263472 A | 10/2006 |
| | (Continued) | |

OTHER PUBLICATIONS

Janusz Siebert et al., "Stroke Volume Variability and Heart Rate Power Spectrum in Relation to Posture Changes in Healthy Subjects", Medical Science Monitor, vol. 10, No. 2, Feb. 1, 2004, pp. MT31-MT37.

(Continued)

*Primary Examiner* — Tiffany Weston
*Assistant Examiner* — Tho Tran
(74) *Attorney, Agent, or Firm* — Squire Patton Boggs (US) LLP

(57) ABSTRACT

Method and system for monitoring stress level of a subject. Beat-to-beat time variation and stroke volume variation of the heart a subject are obtained simultaneously, and a stress level indication is determined as a function of the beat-to-beat time variation and the relative stroke volume variation. More accurate and reliable estimates for stress level may be obtained.

25 Claims, 3 Drawing Sheets

(56) References Cited

U.S. PATENT DOCUMENTS

| | | | |
|---|---|---|---|
| 2004/0092835 A1* | 5/2004 | Yasushi | A61B 5/02405 600/513 |
| 2004/0249297 A1* | 12/2004 | Pfeiffer | A61B 5/02028 600/526 |
| 2008/0071181 A1 | 3/2008 | Stabler et al. | |
| 2008/0161877 A1* | 7/2008 | Kirby | A61N 1/3601 607/42 |
| 2009/0099424 A1* | 4/2009 | O'Brien | A61B 5/02028 600/301 |
| 2009/0124867 A1 | 5/2009 | Hirsh et al. | |
| 2011/0066042 A1 | 3/2011 | Pandia et al. | |
| 2012/0277603 A1 | 11/2012 | Camenzind et al. | |
| 2014/0107493 A1 | 4/2014 | Yuen et al. | |

FOREIGN PATENT DOCUMENTS

| | | |
|---|---|---|
| JP | 2007130181 A | 5/2007 |
| JP | 2013511350 A | 4/2013 |
| WO | WO 2008/045995 A2 | 4/2008 |
| WO | 2011068687 A1 | 6/2011 |

OTHER PUBLICATIONS

Beverly J. Volicer and Ladislav Volicer, "Cardiovascular Changes Associated with Stress During Hospitalization", Journal of Psychosomatic Research, vol. 22, Jan. 1, 1978, pp. 159-168.

Ze Zhao et al., "Spectral and Coherence Analysis of the Variabilities of Heart Rate, Stroke Volume, and Systolic Blood Pressure in Exercise Stress Tests", International Conference on Biomedical and Health Informatics (BHI 2012), Jan. 2-7, 2012, pp. 771-774.

International Search Report application No. PCT/IB2015/055576 dated Oct. 28, 2015.

Finnish Search Report dated Mar. 13, 2015 corresponding to Finnish Patent Application No. 20145694.

Zhao et al., "Spectral and Coherence Analysis of the Variabilities of Heart Rate, Stroke Volume, and Systolic Blood Pressure in Exercise Stress Tests," Conference Proceeding Article of IEEE-EMBS International Conference on Biomedical and Health Informatics, pp. 771-774, Jan. 5, 2012.

Kusserow et al., "Monitoring Stress Arousal in the Wild," IEEE Pervasive Computing, vol. 12, No. 2, pp. 28-37, Apr. 1, 2013.

* cited by examiner

METHOD AND SYSTEM FOR MONITORING STRESS

BACKGROUND

Field

The present invention relates to monitoring vital signs of a subject and especially to a system, method and a computer program product for monitoring a level of stress of a subject.

Description of the Related Art

Stress may be defined as a state of bodily or mental tension resulting from factors that tend to after an existent equilibrium (Merriam-Webster's Online Dictionary). In recent years, it has become increasingly important both from wellness and from athletic training point of view to have a good and reliable picture of the level of one's physiological and/or mental stress, and recovery of it. This may be especially important for optimal training in endurance sports.

Heart rate variability (HRV) refers to a variation in the beat-to-beat interval of the heart. Variation in the beat-to-beat interval is a physiological phenomenon; the sinoatrial node of the heart receives several different inputs, and the instantaneous heart rate and its variation are results of these inputs. Recent studies have increasingly linked high HRV to good health and a high level of fitness, whilst decreased HRV is associated to stress and tiredness. In various applications, stress and recovery from stress has been thus estimated by measuring HRV from beat-to-beat intervals of the heart.

Many stress and recovery monitoring applications use an ECG (electro cardiogram) technique to measure beat-to-beat intervals of the heart of a subject, and HRV is determined from these measured values. It is known that a naturally occurring primary fluctuation in the heart rate occurs because of breathing, but despite many studies, precise mechanisms of respiration-induced heart rate variations are still not fully known. The monitoring applications include various HRV analysis methods, but many challenges still exist.

An example of a situation where an error may occur is overnight recovery analysis, e.g. for athletes. FIG. 1 illustrates heart rate and heart rate variability of a person in an overnight measurement. It may be seen that during the phase of falling asleep the depth of respiration and the variability of respiration rate decrease, and along with them also the heart rate variability decreases. This tends to lead to an erroneous judgment of increased stress, although the opposite happens.

To make individual results comparable, some simple commercial training applications instruct their users to measure HRV daily in similar conditions (e.g. in the morning). This eliminates some of the effect of respiration to the measurements, but similarity of relevant conditions is difficult to verify, and therefore the results are reliable only to an extent. In other type of training applications, users are requested to provide manually input additional data related to their pre-measurement activity, and this additional data is used to improve interpretation of the measured HRV values. Such methods are more accurate, but laborious to the users. Furthermore, they are still indirect, i.e. the interpretation is based on experimental and averaged statistical data.

There are also applications that use advanced mathematical analysis methods to determine the level of stress from measured beat-to-beat intervals. For example, frequency-domain methods assign bands of frequency and divide measured beat-to-beat intervals to them. Stress level is then derived from distribution of the measured intervals across these frequency bands. In time-domain methods beat-to-beat intervals are statistically analyzed to give variables, such as standard deviation, root mean square of successive differences, etc. These methods may provide more accuracy, but require a lot of computing. And still, interpretation of the computed distributions and variables is indirect, i.e. based on experimental and averaged data.

SUMMARY

An object of embodiments of the present invention is to provide an improved stress monitoring where at least one of the disadvantages of the prior art is eliminated or alleviated. The objects of the present invention are achieved with a system, method and computer program product as described herein.

Embodiments of the invention apply an understanding that variation of stroke volume of the heart is modulated by respiration of the subject, but it is quite minimally influenced by physiological or mental stress. Accordingly, when stroke volume is measured in parallel with beat to beat times of the heart, it is possible to separate by far the effect of respiration and the effect of physical and psychological stress from the measured values. This means that a more accurate and reliable estimate for stress level may be obtained.

BRIEF DESCRIPTION OF THE DRAWINGS

In the following, embodiments of the invention will be described in greater detail, with reference to the attached drawings, wherein.

DETAILED DESCRIPTION

The following embodiments are exemplary. Although the specification may refer to "an", "one", or "some" embodiment(s), this does not necessarily mean that each such reference is to the same embodiment(s), or that the feature only applies to a single embodiment. Single features of different embodiments may be combined to provide further embodiments.

In the following, features of the invention will be described with an example of a device architecture in which various embodiments of the invention may be implemented. Only elements relevant for illustrating the embodiments are described in detail.

A monitoring system according to embodiments of the invention generates one or more output values for one or more parameters that are indicative of stress, or recovery from stress of a subject. These values may be used as such or be further processed to indicators of stress, or recovery from stress of the subject. The monitoring system is herein disclosed as applied to a human subject. The invention is, however, applicable to animal species or any type of a subject with a heart.

The invention includes obtaining simultaneously beat-to-beat time variation and stroke volume of the subject. Beat-to-beat time variation or heart rate variability (HRV) refers here to the physiological phenomenon of variation in the time interval between heartbeats of a subject. Methods to detect beats include, for example, electrocardiography (ECG), blood pressure measurements with sphygmomanometers, ballistocardiological devices, and pulse wave signal measurements with photoplethysmographs (PPG) or pressure sensors.

Stroke volume (SV) refers here to a volume of blood pumped from one ventricle of the heart with each beat. The stroke volume may be calculated from measurements of ventricle volumes by subtracting the volume of blood in the ventricle at the end of a beat (called end-systolic volume) from the volume of blood just prior to the beat (called end-diastolic volume). Methods to detect stroke volumes include echocardiograms, ballistocardiological devices, and pulse wave signal measurements with photoplethysmographs (PPG) or pressure sensors. Stroke volume variation (SVV) refers here to the physiological phenomenon of variation in the stroke volume in a subject.

Embodiments of the present invention include a device that includes means for measuring simultaneously beat-to-beat time variation and stroke volume variation of a subject. Depending on applied methods for detecting heartbeats or stroke volumes, one single sensor, or separate sensors for measuring SSV and HRV may be used.

Figure 1:
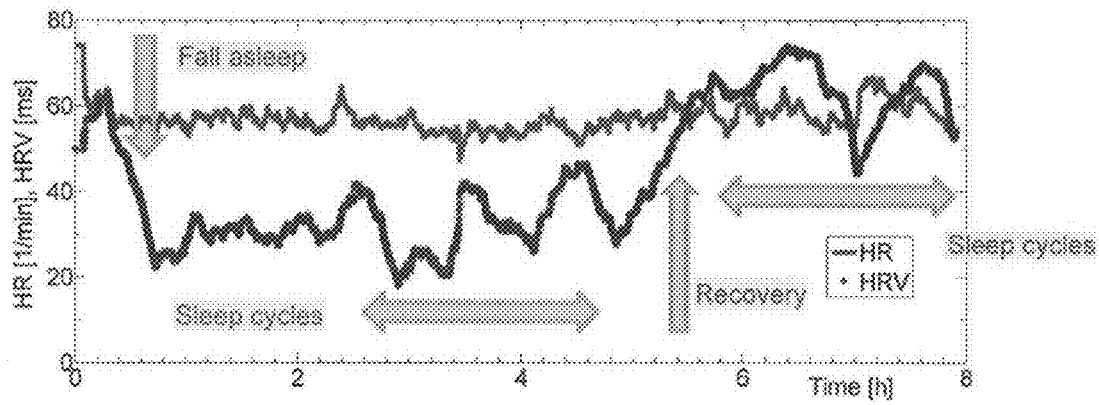
FIG. 1 illustrates heart rate variability of a person in an overnight measurement.
Figure 2:
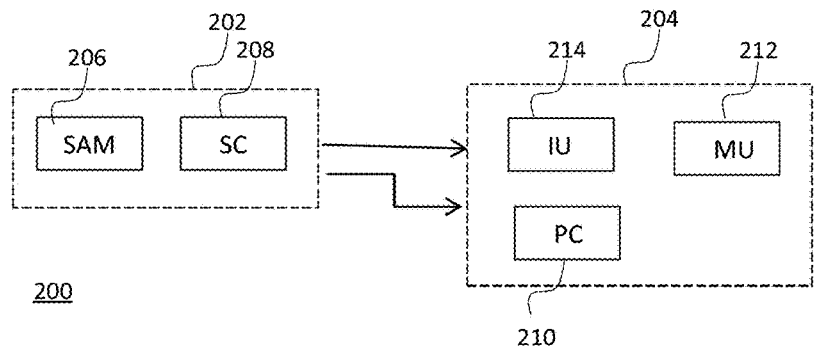
FIG. 2 illustrates functional elements of an embodiment of a monitoring system.

FIG. 2 illustrates functional elements of an embodiment of a monitoring system 200 according to the present invention. The monitoring system 200 gives an example of a configuration that includes a sensor configured to obtain a ballistocardiologic signal that is indicative of both stroke volumes and beat-to-beat times of the heart of a subject. The monitoring system 200 includes signal processing means configured to generate from the ballistocardiologic signal measured values of an output parameter that is indicative of stress or recovery from stress of the subject. These elements may be implemented as one physical device or two or more electrically or communicatively coupled physical devices of the system.

FIG. 2 illustrates an exemplary configuration where the monitoring system 200 comprises a sensor unit 202 and a control unit 204. The sensor unit 202 may be considered as an element to be attached to the monitored subject and the control unit 204 may be considered as an element communicatively coupled to the sensor unit 202 but physically detached from the monitored subject. The sensor unit 202 may be directly attached to or pressing on the monitored subject, or it may be placed to indirectly obtain a ballistocardiologic signal from an element attached to or pressing on the subject, e.g. a bed or a chair.

The sensor unit 202 includes one or more sensors 206 for obtaining a ballistocardiologic signal. Ballistocardiology refers in general to a technology for measuring movements of a body, which are caused in response to shifts in the center of the mass of the body during heartbeat cycles. The sensor may sense linear or angular motion of the body and thus be, for example, an accelerometer, or a gyroscope.

The sensor unit 202 may also include a signal conditioning unit 208 that manipulates the raw input electrical signal to meet requirements of a next stage for further processing. Signal conditioning may include, for example, isolating, filtering, amplifying, and converting a sensor input signal to a proportional output signal that may be forwarded to another control device or control system. A signal conditioning unit 208 may also perform some computation functions such as totalization, integration, pulse-width modulation, linearization, and other mathematical operations on a signal. The signal conditioning unit 208 may alternatively be included in the control unit 204.

In case a sensor of angular motion is used, the sensor unit can be attached to the chest of the subject from which the rotational movement of the heart at every heart beat can be detected and obtained. In linear detection, the sensor unit is also advantageously attached directly to the subject, but the sensor unit may alternatively be attached indirectly, for example to a bed where the subject rests in, to a chair or seat where the subject sits, to a bathroom scale where the subject stands, or the like. An accelerometer may be used to detect the recoil signal of the blood moving in the veins from the movement transferred to the intermediate item (e.g. the bed or chair) from the body.

The control unit 204 is communicatively coupled to the sensor unit to input signals generated by the sensor for further processing. Typically the coupling is electrical, allowing both a power supply to the sensor unit, as well as wireline exchange of signals between the sensor unit and the control unit. The sensor unit may, however, be a standalone unit with own power supply and radio interface to the control unit. On the other hand, the sensor unit and control unit may be implemented as one integrated physical device.

The control unit 204 is a device that comprises a processing component 210. The processing component 210 is a combination of one or more computing devices for performing systematic execution of operations upon predefined data. The processing component may comprise one or more arithmetic logic units, a number of special registers and control circuits. The processing component may comprise or may be connected to a memory unit 212 that provides a data medium where computer-readable data or programs, or user data can be stored. The memory unit may comprise one or more units of volatile or non-volatile memory, for example EEPROM, ROM, PROM, RAM, DRAM, SRAM, firmware, programmable logic, etc.

The control unit 204 may also comprise, or be connected to an interface unit 214 that comprises at least one input unit for inputting data to the internal processes of the control unit, and at least one output unit for outputting data from the internal processes of the control unit.

If a line interface is applied, the interface unit 214 can include plug-in units acting as a gateway for information delivered to its external connection points and for information fed to the lines connected to its external connection points. If a radio interface is applied, the interface unit 214 typically comprises a radio transceiver unit, which includes a transmitter and a receiver. A transmitter of the radio transceiver unit may receive a bitstream from the processing component 210, and convert it to a radio signal for transmission by an antenna. Correspondingly, the radio signals received by the antenna may be led to a receiver of the radio transceiver unit, which converts the radio signal into a bitstream that is forwarded for further processing to the processing component 210. Different line or radio interfaces may be implemented in one interface unit.

The interface unit 214 may also comprise a user interface with a keypad, a touch screen, a microphone, or equals for inputting data and a screen, a touch screen, a loudspeaker, or equals for outputting data to a user of the device.

The processing component 210 and the interface unit 214 are electrically interconnected to provide means for performing systematic execution of operations on the received and/or stored data according to predefined, essentially programmed processes. These operations comprise the procedures described herein for the control unit of the monitoring system of FIG. 2.

Figure 3:
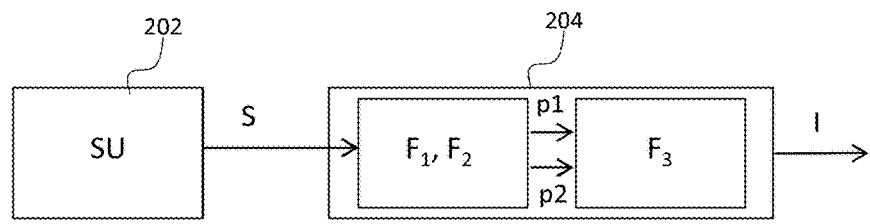
FIG. 3 illustrates functional configuration of a stress monitoring system.

FIG. 3 illustrates functional configuration of the stress monitoring system 200 that includes the sensor unit 202 and the control unit 204 of FIG. 2. The sensor unit, when in direct or indirect contact with the subject, is exposed to the recoil motion of the body during heartbeat cycles. In response to this movement the sensor generates a ballistocardiologic signal and forwards it to the control unit. The control unit includes data processing functions $F_1$, $F_2$, each of which defines a rule or correspondence between values of the ballistocardiologic signal and values of output parameters p1, p2 that are indicative of operational parameters of the heart of the subject. In the exemplary embodiment of FIG. 2, the first function F1 results in values of parameter p1 representing beat-to-beat time variation of the heart of the subject. The second function F2 results in values of parameter p2 representing stroke volume variation of the heart of the subject. The control unit includes also a data processing function F3 that defines a rule of correspondence between simultaneously measured values of parameters p1 and p2 and at least one value of an output parameter I that indicates stress level of the monitored subject. The control unit 204 may store values of the output parameter I to a local data storage for later processing, output it in one or more media forms through the user interface of the control unit, and/or transmit it to a remote node for further processing.

Figure 4:
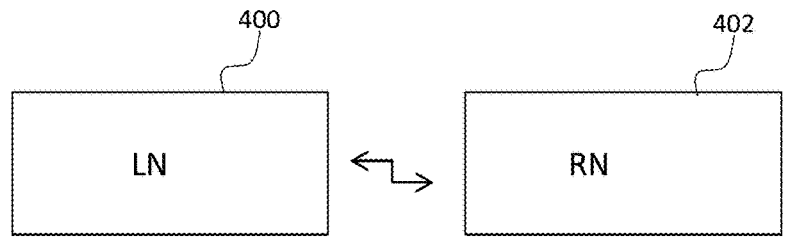
FIG. 4 illustrates a remote monitoring system.

FIG. 4 illustrates a remote monitoring system including the monitoring system of FIG. 2. The system may include a local node 400 that comprises the sensor unit 202 and the control unit 204 of FIG. 2. In addition, the local node 400 may be communicatively connected to a remote node 402. The remote node 402 may be, for example, an application server that provides a monitoring application as a service to one or more users. One of the aspects monitored with the application may be the level of stress of the user. Alternatively, the remote node may be a personal computing device into which a stress monitoring application has been installed. The local node may be a dedicated device or combination of devices including the sensor unit and the control unit described above. Alternatively, the local node may be implemented as a sensor unit that interfaces a client application in a multipurpose computer device (for example a mobile phone, a portable computing device, or network terminal of a user). A client application in the computer device may further interface the sensor unit and a server application. The server application may be available in a physical remote node 402, or in a cloud of remote nodes accessible through a communication network.

While various aspects of the invention may be illustrated and described as block diagrams, message flow diagrams, flow charts and logic flow diagrams, or using some other pictorial representation, it is well understood that the illustrated units, blocks, apparatus, system elements, procedures and methods may be implemented in, for example, hardware, software, firmware, special purpose circuits or logic, a computing device or some combination thereof. Software routines, which may also be called as program products, are articles of manufacture and can be stored in any apparatus-readable data storage medium, and they include program instructions to perform particular predefined tasks. Accordingly, embodiments of this invention also provide a computer program product, readable by a computer and encoding instructions for monitoring stress levels, or recovery from stress of a subject in a device or a system of FIG. 2, 3, or 4.

As discussed above, a signal that is indicative of both stroke volumes and beat-to-beat times of the heart of a subject can alternatively be obtained with a pulse wave measurement device. Such device comprises a fastening element for detachably attaching a pressure sensor to a position on the outer surface of a subject. The pressure sensor may be configured to generate a pulse wave signal that varies according to deformations of the tissue in response to an arterial pressure wave expanding or contracting a blood vessel underlying the tissue in the position. A processing component is configured to input the pulse wave signal and compute from it pulse wave parameters that represent stroke volumes and beat-to-beat times of the heart of a subject.

Applied sensors can be, for example, microelectromechanical devices, but other detection technologies may be applied, as well. A single sensor for measuring both stroke volumes and beat-to-beat intervals can be used since it reduces costs and simplifies processing of the two types of parameters. However, the invention may be implemented also with configurations that generate two separate signals, as long as simultaneous detection is possible.

Figure 5:
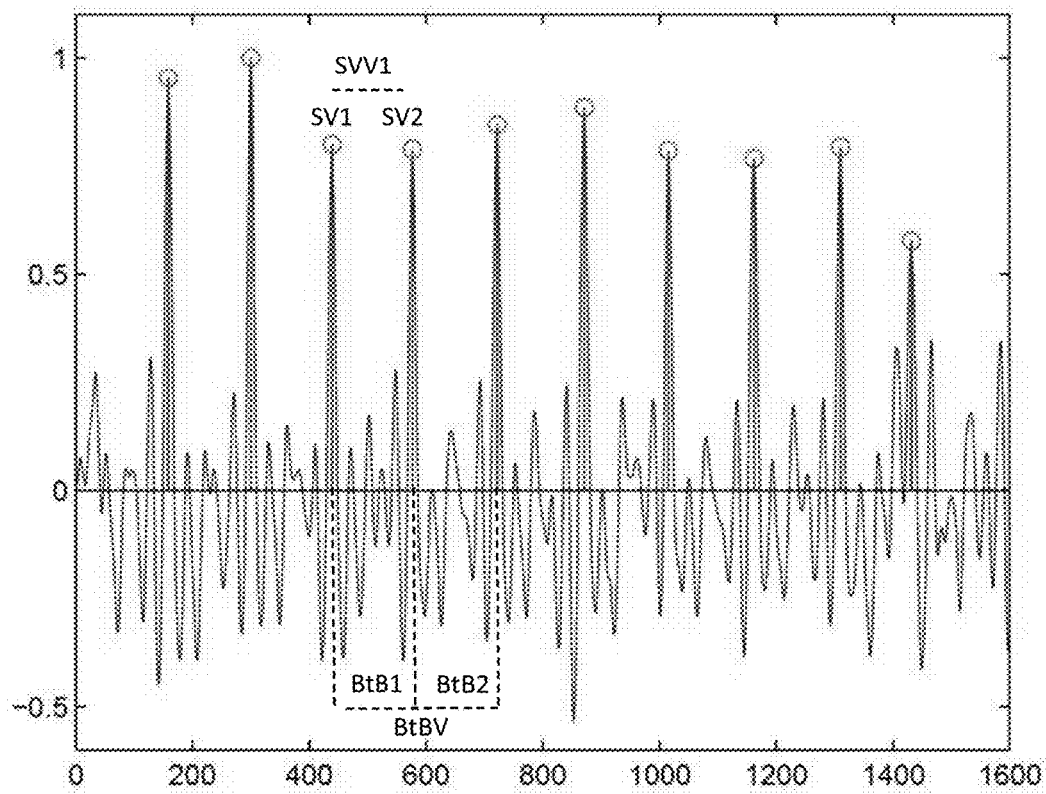
FIG. 5 illustrates an exemplary filtered angular ballistocardiologic signal during heartbeat cycles of a test subject.

Simultaneity in this context is associated to periodic nature of the signal or signals, following the cardiac cycle of the subject. FIG. 5 illustrates an exemplary filtered angular ballistocardiologic signal S during heartbeat cycles of a test subject. The vertical axis represents the magnitude of sensed angular rate in a specific sense direction, and the horizontal axis represents accumulated number of time steps or elapsed time. The control unit may be configured to generate values for various output parameters, for example, a parameter may be indicative of the stroke volume of the heart of the subject. The output parameter for stroke volume may be generated by determining amplitude of the angular ballistocardiologic signal S and using that as a value to represent the temporal stroke volume. For example, a peak amplitude, semi-amplitude, or root mean square amplitude may be used for the purpose. Since the signal is not a pure symmetric periodic wave, amplitude is advantageously measured in respect to a defined reference value, for example, from a zero point of the signal curve. Other reference values may be applied within the scope, as well. Values for stroke volume variation may then be computed as a difference between two successive temporal stroke volume values.

Alternatively, or additionally, a parameter may be indicative of the heartbeat of the subject. For example, the output parameter may be generated by selecting a characteristic point of the angular ballistocardiologic signal S and determining the occurrence of the characteristic point in consecutive signal sequences. For example, a minimum or maximum value of the signal sequence may be applied as the characteristic point. The occurrence of the characteristic point may be considered as a time stamp of the heartbeat. A period between two timestamps may be considered to represent temporary beat-to-beat (B-B) time of the heart of the subject, and inverse of this to represent heart rate (HR) of the subject. Values for beat-to-beat interval variation may then be computed as a difference between two successive heart rate values.

Similar methods may be used with pulse wave signals; amplitudes of the wave may be applied to determine stroke volumes and periods between characteristic points of successive waves to determine beat-to-beat intervals.

In both the stroke volume and the beat-to-beat time variation determination, a specific period of a measured signal is applied. In stroke volume measurements, the amplitude may be determined between a zero point and maximum value at a point of time of the signal curve period. On the other hand, even the whole signal curve period may be applied to compute averaged amplitude values. Partial signal periods between these two examples may be applied as well, depending on the selected amplitude determination mechanism. Beat-to-beat time may be determined from an interval between characteristic points in two successive signal curve periods. Computation of variation of the beat-to-beat times may thus involve two or more successive periods of the signal curve.

In the invention, beat-to-beat time variation and relative stroke volume variation of a subject are obtained simultaneously and a stress level indication SI is determined as a function of the beat-to-beat time variation and relative stroke volume variation. In this context, the stroke volume variation and beat-to-beat time variation can be considered to be obtained simultaneously when an interval or intervals applied to determine a value for stroke volume variation and an interval or intervals applied to determine a value for beat-to-beat time variation for determination of a value for a stress level indication at least partly overlap in time.

The concept of simultaneous measurements is illustrated with an example in FIG. 5. FIG. 5 shows a simplified exemplary computation method where temporal stroke volumes SV1, SV2 are computed from a difference between a zero point of the signal curve and a maximum point of the signal period. Temporal beat-to-beat times BtB1, BtB2 are computed from an interval between maximum points of two successive signal periods. Stroke volume variation SVV1 may be then computed from the difference of temporal stroke volumes SV1, SV2, and beat-to-beat interval variation BtBV from the difference between temporal beat-to-beat times BtB1, BtB2. Intervals applied to determine a value for stroke volume variation and to determine a value for beat-to-beat time variation are marked in FIG. 5 with horizontal dashed lines. It is seen that these intervals at least partly overlap in time and may be applied for determination of a value of a stress level indication SI. Application of this principle to configurations using other signal types or two separate signals is clear to a person skilled in the art.

An option of obtaining beat-to-beat time variation is low pass filtering absolute values of consecutive beat-to-beat time differences. One possible filter function is:

$$y(t)=y(t-1)*(1-k)+x(t)*k,$$

where $x(t)=ABS(tb2b(t)-tb2b(t-1))$ and $y(t)$ and $y(t-1)$ are the beat-to-beat times at time steps t and t−1 respectively, and k<1 is a filter coefficient. tb2b(t) and tb2b(t−1) are beat-to-beat times at time steps t and t−1 respectively.

An option of calculating the relative stroke volume variation is:

$$SVV(t)=SVV(t-1)*(1-k)+k*x(t)$$

where SVV(t) and SVV(t−1) are the relative stroke volume variation at time steps t and t−1 respectively, k<1 is a filter factor and $x(t)=ABS(SV(t)-SV(t-1))/AVE\_SV(t)$, where SV(t) and SV(t−1) are the stroke volume at time steps t and t−1 respectively and AVE_SV(t) is a low pass filtered stroke volume function. The filter may for example be of the same form as the filter used for filtering beat-to-beat times above, i.e.

$$y(t)=y(t-1)*(1-k)+x(t)*k,$$

where x(t) is a raw stroke volume and y(t) low pass filtered stroke volume.

It is known that both the stroke volume and the beat-to-beat rate vary by respiration of the subject, but the beat-to-beat time variation is significantly influenced by mental and physiological stress, whereas the stroke volume variation is mainly influenced by the depth of respiration. The possibility of measuring stroke volume variation in parallel with beat-to-beat time variation enables separation of the effect of physical or psychological stress and recovery from the measured values. An accurate stress indication can thus be obtained directly from one or two sensor data signal inputs with minimal computation.

Let us denote a stress level indication SI to represent an indication of the level of mental and physiological stress experienced by the subject. SI may be computed as a function of measured beat-to-beat time variation (HRV) and stroke volume variation (SVV):

$$SI=f(HRV;SVV)$$

For the purpose of SI calculations, it is possible to assume that during an applicable measurement duration (minutes to hours), changes in the relation of the beat-to-beat time variability (HRV) and stroke volume variation (SVV) are stress-related. A simple example for of a function that may be used for computing SI is:

$$SI=HRV/SVV$$

Accordingly, in the absence of stress, the relation of the two parameter values can be assumed to remain within a defined range. Deviations from this range, especially the HRV becoming smaller than SVV, can be considered to indicate increased stress levels.

Another possibility is to use a function:

$$SI=HRV/(SVV/SV),$$

where SV is an average stroke volume of the subject during the measurement.

It is also possible to use other types of functions, for example functions where compensation of the effect of respiration is attenuated or non-linear, i.e.

$$SI=HRV/(1+k*SVV/SV)$$

or $$SI=HRV/(SVV/SV)\hat{}k$$

wherein k is a coefficient.

In analysis, the heart rate variability (HRV) may be differentiated in the spectral profile into the high frequency (HF) band (0.10 to 0.40 Hz), the low frequency (LF) band (0.04 to 0.10 Hz), and the very low frequency (VLF) band (<0.04 Hz). The variation in the heart rate, caused by the breathing cycle, is typically detected in the high frequency (HF) band. The low frequency (LF) band (0.04 to 0.10 Hz) represents oscillations related to regulation of blood pressure and vasomotor tone including the so-called 0.1 Hz fluctuation. Heart rate variability in the low frequency (LF) band is herein referred to as low frequency heart rate variability (LFHRV), and heart rate variability in the high frequency (HF) band as high frequency heart rate variability (HFHRV). In an embodiment, the applied function may be:

$$SI=HFHRV/(LFHRV*SVV/SV)=(HFHRV*SV)/(LFHRV*SVV)$$

Figure 6:
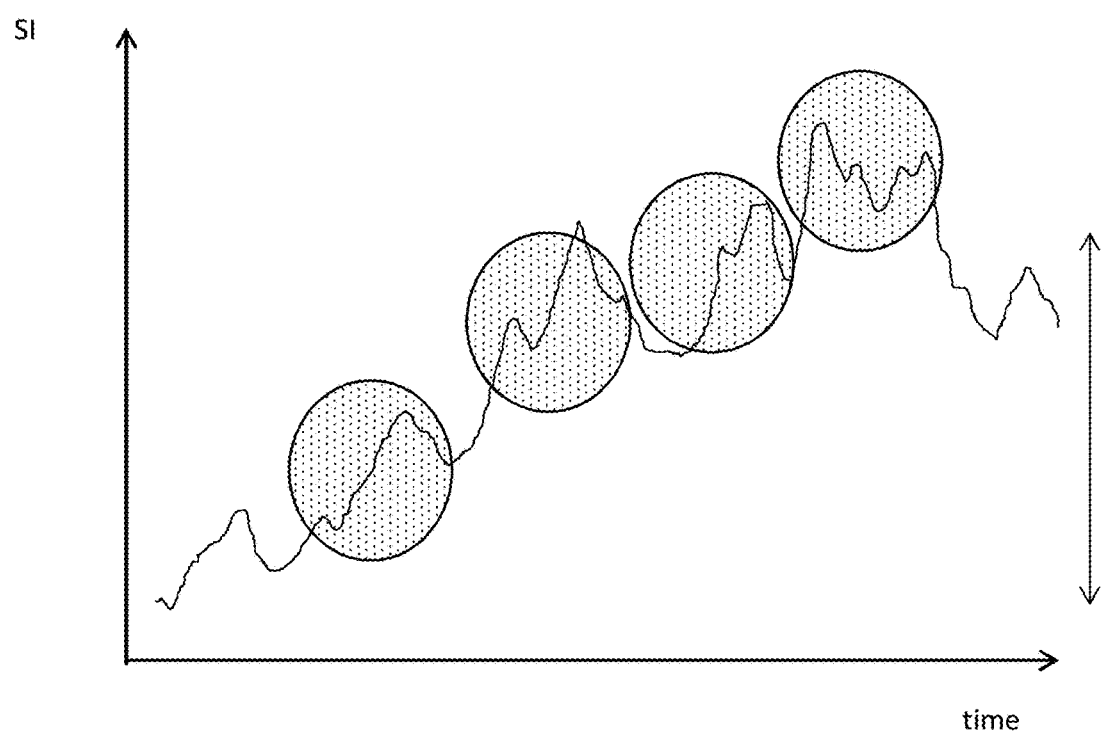
FIG. 6 illustrates a sleep cycle curve of a subject in a test situation.

Use of this function provides a good estimate on temporary stress levels. In addition, it has been detected that variations of the SI by far correspond to the sleep cycles of the subject. Accordingly, the proposed method enables also an easy and unobtrusive way to detect sleep cycles of the subject. FIG. 6 illustrates an exemplary curve resulting from digital filtering of the signal of SI with a filter $$y(n)=y(n-1)*(1-k)+k*x(n)$$

wherein the time factor is between 10 to 20 minutes. Other filters may naturally be applied within the scope. The patterned circles illustrate sleep cycles of the subject. As earlier, the stress level indication applied in this example may be considered to describe the level of recovery during the monitored interval so that the rising stress level indication curve indicates temporary recovery levels that get higher along with the successive sleep cycles.

An indication of the sleep cycles may be output, for example, by displaying it to a monitoring personnel in a display unit, or by transferring it to another unit that further processes the sleep cycle data for monitoring indications or alarms.

In an embodiment of the invention the ballistocardiologic signal is obtained by an accelerometer or a force or pressure sensor. A heartbeat of a subject results in blood flowing in the body of the subject, resulting in a measureable force. First or second derivatives of this measured force by a sensor may be used for determining the heart rate variability (HRV). Derivation of the obtained force signal will result in an acceleration signal. The effect of acceleration caused by the subject moving or from other external sources may be reduced by low pass filtering the obtained acceleration signal to a relevant bandwidth. Both analogue and digital filters may be used, e.g. using function:

$$y(t)=y(t-1)*(1-k)+x(t)*k,$$

where y(t) and y(t−1) are the filter outputs at time steps t and t−1 respectively, x(t) is the filter input at time step t and k is a filter coefficient.

The heartbeat may then be detected by requiring that for a detected heartbeat the filtered function fulfils one or more of the following criteria. The applied criteria compare a sequence of successive maxima and minima to a preset threshold value:
- a sequence of three minima and maxima, min1->max1->min2->max2->min3->max3, where the sum of the slopes=(max1−min1)+(max1−min2)+max2−min2)+(max2−min3)+(max3−min3) exceeds a preset limit,
- a sequence of max->min->max, where the sum of the slopes e.g. =(max1−min2)+(max2−min2) exceeds a preset limit,
- a sequence of min->max->min, where the sum of the slopes e.g. =(max2−min2)+(max2−min3) exceeds a preset limit.

If one or more of the criteria is fulfilled, a heartbeat is detected. One of the applied maxima or minima (e.g. max1) may be selected as a timestamp of the detected heartbeat. Based on these individual heart beat timestamp, beat-to-beat time intervals and therefrom beat-to-beat time variations may be calculated, as described above.

For further improvement, incorrect time intervals may be removed and missing intervals may be filled in by means of a plausibility criteria. For example:
- derived beat-to-beat times shorter than those corresponding to the maximum heart rate of the population, or corresponding to the heart rate of the subject measured, or shorter than those corresponding to the population or the subject under the conditions where the measurement takes place (e.g. standing on a scale), are removed, and
- changes of beat to beat-to-beat times larger than those possible for the population or the subject in question are not accepted.

After use of the plausibility criteria, plausible heart beats remain, and heart rate variation and may be accurately calculated, for example, for corresponding recovery or stress level determinations. For this, the measured residual signal may be double integrated to obtain heart beat impulse, beat volume and cardiac output values. It is noted, however, that this method of detecting heartbeats based on simple calculations with a sequence of successive maxima and minima is independently applicable for heartbeat detection in other applications, as well. For example, the method may be applied to detect the presence of humans or animals in vehicles or hospital beds or guarded facilities, for example. The disclosed method requires minimal computing resources and is therefore applicable to various environments, including mobile applications.

A stress level indication that results from the disclosed monitoring stress level of a subject may be applied as such by displaying the result through the interface unit of the monitoring system to the subject, or to another person, for example to one that monitors well-being of the subject. An visual indication of the stress level already provides important information on sleep quality and recovery for athletes, but analysis of sleep quality and recovery from efforts is equally important to anyone at any stage of life. The proposed method can be used to monitor stress levels of a foetus, and thereby enable early detection of abnormal conditions during the pregnancy. The visual stress level indication is applicable to express abnormal states also in later stages of life, especially in infancy and at old age.

It is also possible to apply the stress level indication without or in addition to a display function. The stress level indication can be used for further processing in a monitoring system where additional signals and/or physiological parameters of the subject are available. The stress level indication can, alone or in combination with other physiological parameters be used to give an early warning of pathological conditions, such as infections or inflammations, cardiac infarction, atrial fibrillation or an increased risk of sudden infant death syndrome.

It is apparent to a person skilled in the art that as technology advances, the basic idea of the invention can be implemented in various ways. The invention and its embodiments are therefore not restricted to the above examples, but they may vary within the scope of the claims.

The invention claimed is:

1. A method for monitoring stress level of a subject, said method comprising:
   attaching a sensor device to a subject;
   simultaneously measuring, with the sensor device, beat-to-beat time variation and a relative stroke volume variation of a heart of the subject;
   outputting the beat-to-beat time variation and the stroke volume variation to a control device that is communicatively coupled to the sensor device;
   determining, by the control device, a stress level indication as a function of the beat-to-beat time variation and the relative stroke volume variation, wherein the function comprises a ratio of beat-to-beat time and stroke volume variations, and wherein the beat-to-beat time and stroke volume variations are simultaneously obtained from the subject; and
   outputting the stress level indication through an interface unit of a monitoring system to indicate a temporary stress level of the subject, using the stress level indication for further processing, and based on the further processing, indicating via the interface unit sleep cycles of the subject, or using the stress level indication for further processing, and based on the further processing, giving an early warning of a pathological condition via the interface unit.

2. The method according to claim 1, wherein the beat-to-beat time variation and the relative stroke volume variation are determined from a sensor signal of the sensor device.

3. The method according to claim 1,
wherein the sensor device comprises a first sensor and a second sensor, and
wherein the beat-to-beat time variation is determined from a sensor signal of the first sensor and the relative stroke volume variation is determined from a sensor signal of the second sensor.

4. The method according to claim 2, wherein at least one of the beat-to-beat time variation and the relative stroke volume variation are obtained from a ballistocardiologic signal generated with an accelerometer or an angular rate sensor.

5. The method according to claim 1, wherein at least one of the beat-to-beat time variation and the relative stroke volume variation are obtained from a blood pressure wave signal generated with a pressure sensor.

6. The method according to claim 1, wherein the beat-to-beat time variation is calculated by low pass filtering absolute values of consecutive beat-to-beat time differences or the stroke volume variation is calculated by low pass filtering consecutive stroke volume value differences.

7. The method according to claim 1, wherein the stress level indication is displayed through a user interface of a monitoring system.

8. The method according to claim 1, wherein the stress level indication is used for further processing in a monitoring system where additional signals or physiological parameters of the subject are available.

9. The method according to claim 1, wherein the stress level indication is computed with the function $$SI = HRV/SVV$$

wherein SI is the stress level indication, HRV is the beat-to-beat time variation, and SVV is the stroke volume variation.

10. The method according to claim 1, wherein the stress level indication is computed with the function $$SI = HRV/(SVV/SV)$$

wherein SI is the stress level indication, HRV is the beat-to-beat time variation, SVV is the stroke volume variation, and SV is an average stroke volume of the subject during a measurement period.

11. The method according to claim 1, wherein the stress level indication is computed with the function $$SI = HRV/(1 + k^* SVV/SV)$$

or $$SI = HRV/(SVV/SV)\hat{0}k$$

wherein SI is the stress level indication, HRV is the beat-to-beat time variation, SVV is the stroke volume variation, SV is an average stroke volume of the subject during a measurement period, and k is a selected coefficient.

12. The method according to claim 1, wherein the stress level indication is computed with the function $$SI = HFHRV/(LFHRV^*SVV/SV) = (HFHRV^*SV)/(LFHRV^*SVV)$$

wherein SI is the stress level indication, LFHRV is the heart rate variability in the low frequency band, HFHRV is heart rate variability in the high frequency band, SVV is the stroke volume variation, SV is an average stroke volume of the subject during a measurement period.

13. The method according to claim 12, further comprising outputting an indication of sleep cycles of the subject computed from the stress level indication signal SI.

14. A computer program product embodied on a non-transitory computer-readable medium, said computer-readable medium encoding instructions which, when run on a computer, executes the method of claim 1.

15. A stress monitoring system, comprising:
a sensor device attached to a subject, the sensor device configured to simultaneously obtain beat-to-beat time variation and a relative stroke volume variation of the heart of the subject; and
a control device configured to determine a stress level indication as a function of the beat-to-beat time variation and the relative stroke volume variation,
wherein the sensor device is further configured to output the beat-to-time variation and the stroke volume variation to the control device that is communicatively coupled to the sensor device,
wherein the function comprises a ratio of beat-to-beat time and stroke volume variations, and wherein the beat-to-beat time and stroke volume variations are simultaneously obtained from the subject, and
wherein the control device is further configured to output the stress level indication through an interface unit of the stress monitoring system to indicate a temporary stress level of the subject, use the stress level indication for further processing, and based on the further processing, indicating via the interface unit sleep cycles of the subject, or use the stress level indication for further processing, and based on the further processing, giving an early warning of a pathological condition via the interface unit.

16. The system according to claim 15, wherein the control device is configured to compute the beat-to-beat time variation and the relative stroke volume variation from one sensor signal of the sensor device.

17. The system according to claim 15,
wherein the sensor device comprises a first sensor and a second sensor, and
wherein the beat-to-beat time variation is determined from a sensor signal of the first sensor, and the relative stroke volume variation is determined from another sensor signal of the second sensor.

18. The system according to claim 15, wherein the system includes an accelerometer or an angular rate sensor, and the determining unit is configured to compute the beat-to-beat time variation or the relative stroke volume variation from a ballistocardiologic signal generated with the accelerometer or the angular rate sensor.

19. The system according to claim 16, wherein the system includes a pressure sensor, and wherein the determining unit is configured to compute the beat-to-beat time variation or the relative stroke volume variation from a blood pressure wave signal generated with the pressure sensor.

20. The system according to claim 18, wherein heartbeats are the detected by comparing a sequence of successive maxima and minima of the ballistocardiologic signal or the blood pressure wave signal to a preset threshold value.

21. The system according to claim 15, wherein the function for computing the stress level indication is $$SI = HRV/SVV$$

wherein SI is the stress level indication, HRV is the beat-to-beat time variation, and SVV is the stroke volume variation.

22. The system according to claim 15, wherein the function for computing the stress level indication is $$SI = HRV/(SVV/SV)$$

wherein SI is the stress level indication, HRV is the beat-to-beat time variation, SVV is the stroke volume variation, and SV is an average stroke volume of the subject during a measurement period.

23. The system according to claim 15, wherein the function for computing the stress level indication is $$SI = HRV/(1 + k*SVV/SV)$$

or $$SI = HRV/(SVV/SV)\hat{0}k$$

wherein SI is the stress level indication, HRV is the beat-to-beat time variation, SVV is the stroke volume variation, SV is an average stroke volume of the subject during a measurement period, and k is a selected coefficient.

24. The system according to claim 15, wherein the function for computing the stress level indication is $$SI = HFHRV/(LFHRV*SVV/SV) = (HFHRV*SV)/(LFHRV*SVV)$$

wherein SI is the stress level indication, LFHRV is the heart rate variability in the low frequency band, HFHRV is heart rate variability in the high frequency band, SVV is the stroke volume variation, SV is an average stroke volume of the subject during a measurement period.

25. The system according to claim 24, wherein the system is configured to output indications of sleep cycles of the subject, each indication of a sleep cycle resulting from digital filtering of the stress level indication signal SI.

* * * * *